United States Patent [19]

Futterer et al.

[11] Patent Number: 5,531,104
[45] Date of Patent: Jul. 2, 1996

[54] DEVICE AND METHOD FOR AUTOMATIC DETECTION OF THE HEIGHT OF SEDIMENTATION IN A SEDIMENTOMETER

[75] Inventors: Manfred Futterer, Frauenfeld; Gerhard Bolli, Berg, both of Switzerland

[73] Assignee: SIA Schweizer Schmirgel, Frauenfeld, Switzerland

[21] Appl. No.: 395,096

[22] Filed: Feb. 27, 1995

[30] Foreign Application Priority Data

Mar. 21, 1994 [CH] Switzerland .............................. 837/94

[51] Int. Cl.⁶ .......................... G01N 15/05; G01N 33/49; G01N 21/00
[52] U.S. Cl. .......................... 73/61.69; 73/61.65; 436/70; 422/82.05
[58] Field of Search ................................ 73/61.69, 61.65; 356/39; 422/82.03, 82.09; 436/70

[56] References Cited

U.S. PATENT DOCUMENTS

| | | | |
|---|---|---|---|
| 3,679,367 | 7/1972 | Negersmith et al. | 73/61.65 |
| 4,118,974 | 10/1978 | Nozaki et al. | 73/61.69 |
| 4,224,405 | 9/1980 | Hijikata | 422/82.09 |
| 4,252,483 | 2/1981 | Haina et al. | 356/39 |
| 4,309,112 | 1/1982 | Ashley et al. | 422/82.09 |
| 4,313,340 | 2/1982 | Schneiwind | 73/61.69 |
| 4,318,296 | 3/1982 | Parker et al. | 73/61.69 |
| 4,848,900 | 7/1989 | Kuo et al. | 356/39 |
| 5,132,097 | 7/1992 | Van Deusen et al. | 422/82.05 |
| 5,316,729 | 5/1994 | Orth et al. | 73/61.69 |

FOREIGN PATENT DOCUMENTS

| | | | |
|---|---|---|---|
| 212781 | 1/1961 | Austria | 422/82.05 |
| 260991 | 10/1988 | German Dem. Rep. | 73/61.69 |
| 165636 | 7/1986 | Japan | 73/61.65 |

*Primary Examiner*—Hezron E. Williams
*Assistant Examiner*—Daniel S. Larkin
*Attorney, Agent, or Firm*—Shoemaker and Mattare Ltd.

[57] ABSTRACT

An illuminating device (6, 7) and a light sensor device (5) are each arranged on opposite sides of the sedimentometer (3). The light sensor device (5) can be adjusted in height by means of a servo-motor (18) and contains two light receivers (11, 13; 12 14) arranged one above the other. The output signals of both light receivers (11, 13; 12, 14) are fed to a controller which activates the servo-motor (18) in such a way that the quantities of light falling on both light receivers (11, 13; 12 14) during the process of sedimentation are maintained at a constant predetermined relationship to one another, with the result that the lower light receiver (12, 14) is constantly maintained at a horizontal alignment with the upper surface of the sediment in the sedimentometer (3). The height adjustment of the light sensor device (5) thus forms a basis of measurement of the height of sedimentation during the sedimentation process. A signal transmitter (20) coupled to the light sensor device (5) transmits a signal which represents the height of sedimentation, the signal being able to be continuously displayed and/or evaluated in a computer. Continuous observation of the sedimentation process is therefore not required.

9 Claims, 1 Drawing Sheet

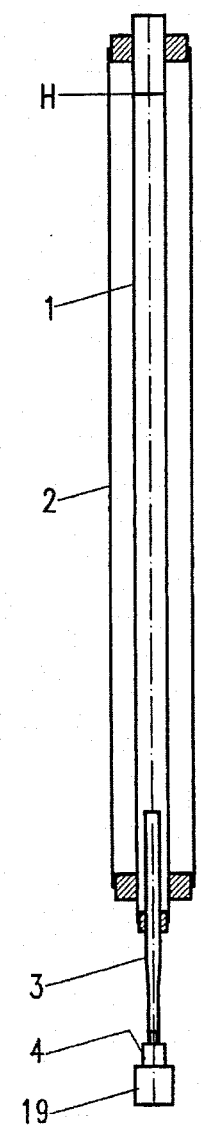
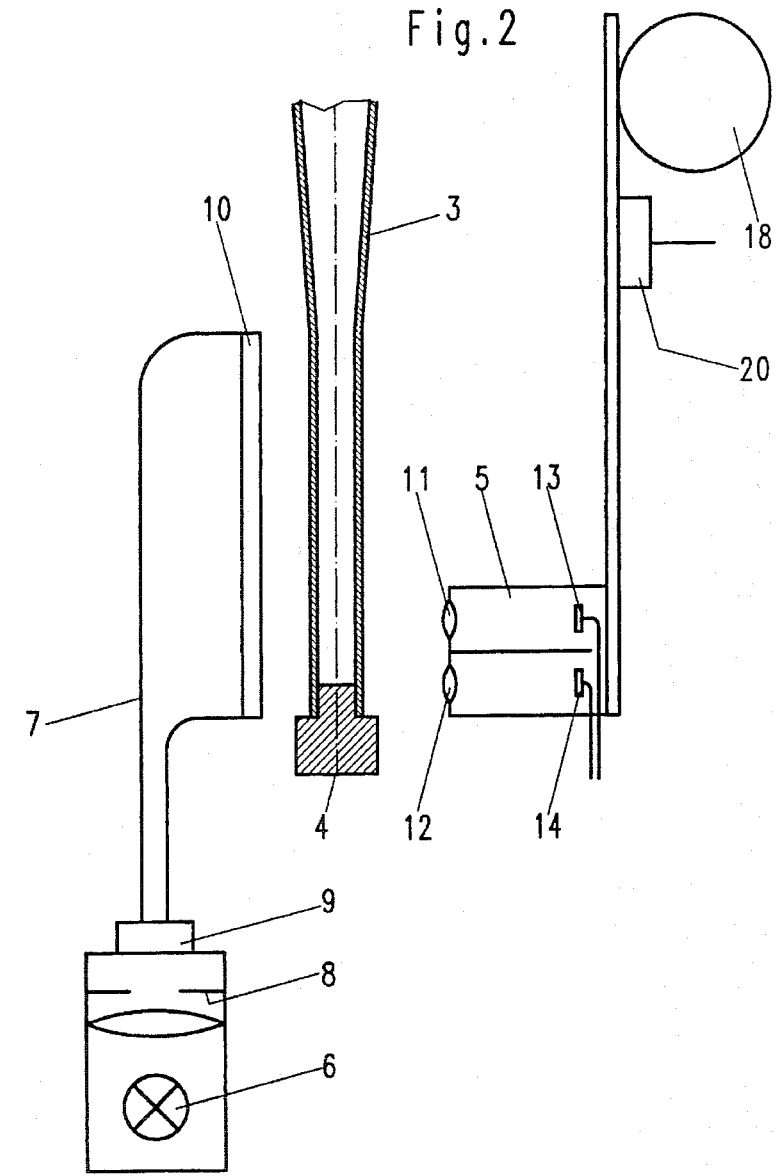
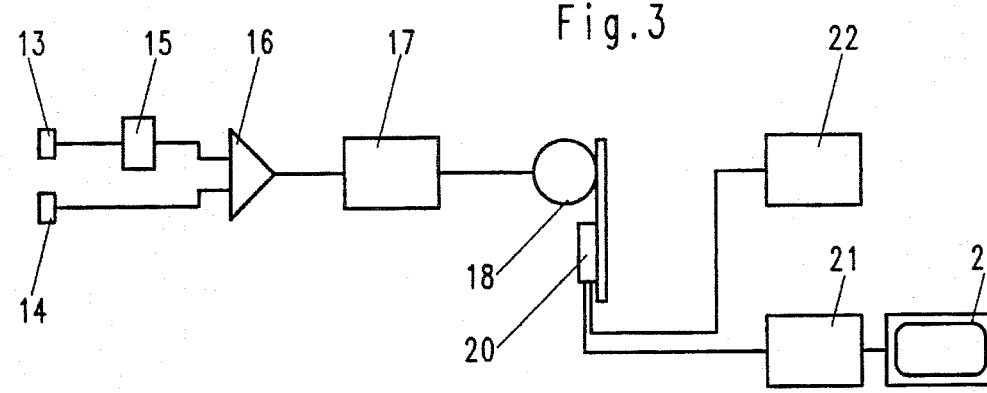

DEVICE AND METHOD FOR AUTOMATIC DETECTION OF THE HEIGHT OF SEDIMENTATION IN A SEDIMENTOMETER

The invention relates to a device and a method for automatic detection of the height of sedimentation during a sedimentation procedure in a sedimentometer.

Sedimentometers are used for the analysis of partical size. Sedimentometers according to the state of the art possess a vertical sedimentation tube filled with a liquid, into the lower end of which a similary vertical collector tube protrudes from below. A sample of analysis material is introduced onto the upper surface of the liquid at a point in time t=0, and the rate of settling of the particles in the liquid is proportional to the square of the diameter d of reference spheres. In a volume of sediment which reaches the closed base of the collector tube after a time t, the equivalent diameter d of the particles is inversely proportional to the square of the settling time t. According to Stokes' Law, particle diameter d can be calculated as follows:

$$d = \frac{k}{\sqrt{t}}$$

In particular, the constant K depends on the viscosity and density of the liquid, as well as the density of the particles.

The standard procedure is to ascertain the times required for specific volumes of sample material to settle on the base of the collector tube. These volumes are obtained by reading off the height of the sediment against a scale marked on the side of the collector tube. After sedimentation is complete, the proportion of the total volume, expressed as a percentage, is calculated for each individual volume, as well as the equivalent diameter d=the latter being calculated from the allocated time t. The percentage distribution of particle size in the sample is thus obtained.

Continous reading of the height of sedimentation in the collector tube against elapsed time is both tedious and time consuming. With fine particled material, sedimentation can last many hours until its conclusion. State of the art experiments in the automation of these analytical methods are based on indirect measurement, where mainly either the cloudiness at different heights or particle size is measured as a basis for deducing the height of sedimentation. These methods are relatively inaccurate.

The purpose of the invention is to create a device and a method with which the height of sedimentation during the process of sedimentation in a sedimentometer is ascertained automatically and with great accuracy.

The device according to the invention which achieves this purpose is characterized by an illuminating device and a light sensor device which are arranged on opposite sides of the sedimentometer, said light sensor device being able to be adjusted in height by means of a servo-motor and possessing two light receivers which transmit output signals to a controller device which in turn actuates the servo-motor in such a way that the quantities of light falling on both the light receivers during the sedimentation process are constantly maintained at a predetermined relationship to one another. This so-called compensation principle allows for filament aging, colour differences in the material to be measured, ambient light etc.

The quantities of light falling upon both light receivers are dependent on the attenuation of light as it passes through the sedimentometer and the liquid or suspension contained therein. Additionally, in relation to the quantity of light falling on the upper light receiver, the quantity of light falling onto the lower of the two light receivers is reduced with regard to the above mentioned predetermined relationship because a portion of the light will be attenuated on its way to the lower light receiver by the sediment in the sedimentometer. By maintaining the above mentioned relationship by means of a controller device, the lower light receiver will constantly be set at the height of the upper limit of the sediment.

The height adjustment of the light sensor device can be measured, registered and evaluated automatically and continuously without difficulty.

The invention is more closely explained in the following, with the aid of the drawings. Namely:

FIG. 1 a schematic vertical section through a sedimentation tube and a collector tube of a sedimentometer, FIG. 2 an enlarged representation of the lowermost end section of the collector tube of the sedimentometer from FIG. 1, and also schematic components of an embodiment of the device according to the invention, and FIG. 3 a diagram of further parts of the device.

According to FIG. 1, a sedimentometer possesses a vertical sedimentation tube 1, filled to a height H with a liquid. The sedimentation tube 1 is surrounded by a water jacket 2 which maintains the sedimentation liquid in the tube 1 at a predetermined, constant temperature. From beneath, a collector tube 3 protrudes into the lower end of the sedimentation tube 1, the upper end of said collector tube being open, while the lower end of said collector tube is closed off by a stopper 4.

Using such a sedimentometer, particle size analysis, for example, can be carried out by introducing a sample of analysis material, suspended in a sedimentation liquid, onto the upper surface of the liquid in the sedimentation tube 1 at point in time t=0, and simultaneously starting a timer. The particles settle in a downward direction in the sedimentation liquid at rates which depend on the sizes of the particles, and eventually settle on the base of the collector tube 3, i.e. on the upper side of the stopper 4.

The device according to the invention automatically and continuously measures the height of the material which has settled on the upper side of the stopper 4 during such a sedimentation procedure. The device contains a light sensor device 5 (FIG. 2) with two light receivers, placed at two positions one above the other, which record light which passes through the collector tube 3 and the liquid or suspension contained therein.

The light emanates from an illuminating device on the side of the collector tube 3 opposite the light sensor device 5, said illuminating device generating a narrow vertical illuminating strip of brightness which is constant over its entire height. In the prefered embodiment as shown, the illuminating device contains a light source 6 which illuminates the input ends of the optical light guides in a bundle of optical light guides 7. A controllable iris diaphram 8, a diffuser 9 for homogenous illumination of the input ends and, if desired, exchangeable coloured filters can be arranged in front of the input ends of the optical light guides. The bundle of optical light guides 7 serves as a cross-sectional adaptor in that, while the input ends of the optical fibres can collectively have a circular cross section, the output ends can form the narrow, vertical illuminating strip as mentioned above. It is practical if a linear-type lens 10 is arranged between the output ends of the optical light guides and the collector tube 3.

An illuminating device with two light guides, preferably however with only a single light source, could be used in place of the above illuminating device, said light guides being moved in conjunction with both the light receivers in a way yet to be described.

Both the light receivers of the light sensor device 5 contain two lenses 11 and 12 arranged one above the other adjacent to the collector tube 3. The upper lens 11 receives light rays leaving the collector tube 3 on an approximately horizontal path, and focusses the light onto an initial light sensitive element 13 within the light sensor device. The lower lens 12 also receives light rays leaving the collector tube 3 on an essentially horizontal path, and focusses the light onto a second light sensitive element 14.

As shown in FIG. 3, the output signal of the initial light sensitive element 13 is fed via a voltage divider 15 to a differential amplifier 16. The output signal of the light sensitive element 14 is fed directly to the differential amplifier 16. The differential amplifier 16 will then always release an output signal when the output signals of the light sensitive elements 13 and 14 which signals are functions of the light intensity falling on each of the elements 13 and 14 do not possess a predetermined relationship as stipulated by the voltage divider 15. The output signal from the differential amplifier 16 is fed to a controller 17 which actuates a servo-motor. The entire light sensor device 5 is arranged to be adjustable in height, and the servo-motor 18 continuously sets the height of the light sensor device 5 so that the quantities of light falling on the light sensitive elements 13 and 14 maintain a predetermined relationship to one another, e.g. a ratio of 2:1. In this case, the quantity of light falling on the second light sensitive element 14 is less than on element 13 because the path of the light ray passing through the lower lens 12 is partially obstructed, for example by 50%, by either the stopper 4 or by the sediment which has settled on the upper side of the stopper 4 during operation. The stopper 4 is opaque and has an even and horizontal upper surface.

In order to carry out particle analysis, as already stated a timer is started at point in time t=0 and a sample of material is introduced onto the upper surface of the liquid in the sedimentation tube 1. The controller device 16, 17 and the servo-motor 18 have set the light sensitive device 5 at commencement of the procedure so that the lower lens 12 is positioned at the height of the upper surface of the stopper 4. The particles settling downwards in the sedimentation liquid cause cloudiness in the liquid which, if said cloudiness reaches the vicinity of the light sensitive device 5, results in attenuation of the light falling upon the light sensitive elements 13 and 14. Since attentuation of light is the same at both of the elements 13 and 14, the relationships between the quantities of light will not change.

It can be observed, however, that the output signal of both light sensitive elements 13 and 14 can reduce very sharply as a result of the attenuation of light, for example by a factor in the order of from between $10^3$ or $10^4$. In practice, therefore, in order to be able to process the signals across such a wide range, the differential amplifier 16 is a logarithmic amplifier.

The largest particles will be the first to settle on the upper surface of the stopper 4, followed by ever smaller particles as the sedimentation procedure continues. At the same time, the height position of the light sensor device 5 will be continously reset by the controller devices 16, 17 and the servo-motor 18 in such a way that the lower lens 12 always remains on the upper surface of the sediment. A standard knocking unit 19 (FIG. 1), which takes effect on the stopper 4, ensures that the upper surface of the sediment remains level during the sedimentation process.

At least one signal transmitter 20 is connected to the light sensor device or to the servo-motor 18. The signal transmitter 20 is activated by the height displacement of the light sensor device 5 in such a way that it dispatches an output signal which represents the actual height of the light sensor device at any time, and thus the height of the sediment which has settled on the upper surface of the stopper 4. The signal transmitter 20 can be an impulse transmitter which dispatches a digital signal representing the travel distance of the light sensor device, said signal being able to be fed to a computer 21 for evaluation. In addition, it is also possible to use a potentiometer as a signal transmitter, which dispatches an analogue output signal. Using this analogue signal, the sedimentation height can be directly plotted against elapsed time as a curve, for example on a recorder 22. Alternatively, a recorder could be mechanically linked directly to the light sensor device 5 in order to produce such a curve.

The computer 21 can evaluate the height of the sediment, as ascertained by means of the light sensor device 5, according to any desired program. It can represent the sedimentation procedure in real-time on a monitor 23, or after completion of a sedimentation process it can chart the cumulative distribution of the particle sizes either linearly or logarithmically, or calculate a particle distribution curve on this basis. The compilation of a table of measurement results or values derived from these results is likewise possible.

In addition, the absolute height of the sediment and thus the density of the sediment can be measured, from which conclusions can be drawn about the sediment.

Inasmuch as the invention is subject to modifications and variations, the foregoing description and accompanying drawings should not be regarded as limiting the invention, which is defined by the following claims and various combinations thereof:

What is claimed is a:

1. Device for automatically ascertaining sediment level in a sedimentometer having a sedimentation tube and a sediment collection tube, said device comprising a light source (6,7) on one side of the collecting tube (3), and a light sensor (5) on an opposite side of the collecting tube (3), and means including a motor (18) for moving the light sensor (5) vertically, said light sensor (5) comprising two light receivers (11, 13; 12,14) arranged one above the other, and a controller (16,17) responsive to outputs from the receivers (11,13; 12,14) and adapted to operate the motor (18) in such a way that the first light receiver (12,14) remains partially obstructed by the sediment, and the quantities of light striking the respective light receivers (11,13; 12,14) are maintained at a constant ratio.

2. Device according to claim 1, wherein the light sensor (5) is connected to at least one signal transmitter (20), the output signal of said transmitter representing the height setting of the light sensor (5).

3. Device according to claim 2, wherein the output signal of the signal transmitter (20) is fed to an evaluation device (22 or 21, 23), said evaluation device representing the height setting as a function of time.

4. Device according to claim 3, wherein the evaluation device (21, 23) contains a computer (21) for ascertaining the cumulative distribution of the particle size of a sample, or a particle distribution curve.

5. Device according to claim 1, wherein the controller (16, 17) contains a logarithmic differential amplifier (16) for the output signals of both the light receivers (11, 13; 12, 14).

6. Device according to claim 1, wherein the light source (6) comprises a cross-sectional adaptor (7) with optical light guides for giving off light in the form of a vertical strip extending longitudinally along the lower section of the sedimentometer (1, 3).

7. Device according to claim 1, wherein the light receivers (11, 13; 12, 14) contain two lenses (11, 12), arranged one above the other, for concentrating light from a respective section of the sedimentometer (1, 3) onto a respective light sensitive element (13, 14).

8. Method of automatically ascertaining the height of sedimentation during the process of sedimentation in a sedimentometer, at least one illuminating device (6, 7) and one light sensor device (5) being arranged each on opposite sides of the sedimentometer (1, 3), the light sensor device being adjusted in height by means of a servo-motor (18) and receiving signals from the direction of the illuminating device by means of two light receivers (11, 13; 12, 14) arranged one above the other, and the output signals of both the light receivers being fed to a controller device (16, 17), said controller being coordinated with the servo-motor (18) in such a way that the quantities of light falling on both the light receivers (11, 13; 12, 14) during the process of sedimentation are constantly maintained at a predermined relationship to one another.

9. Method for automatically ascertaining sediment level in a sedimentometer having a sedimentation tube and a sediment collection tube, said method comprising steps of providing a light source (6,7) on one side of the collecting tube (3), and a light sensor (5) on an opposite side of the collecting tube (3), said light sensor (5) comprising two light receivers (11,13; 12,14) arranged one above the other, and moving the light sensor (5) vertically by means of a controller (16,17) responsive to outputs from the receivers (11,13; 12,14) and in such a way that the first light receiver (12,14) remains partially obstructed by the sediment, and the quantities of light striking the respective light receivers (11,13; 12,14) are maintained at a constant ratio.

\* \* \* \* \*

UNITED STATES PATENT AND TRADEMARK OFFICE
CERTIFICATE OF CORRECTION

PATENT NO.   : 5,531,104
DATED        : July 2, 1996
INVENTOR(S)  : Manford FUTTERER and Gerhard BOLLI It is certified that error appears in the above-identified patent and that said Letters Patent is hereby corrected as shown below:

On title page, item [73]

Change the Assignee from "SIA Schweizer Schmirgel" to to --SIA Schweizer Schmirgel - und Schleifindustrie AG--.

Signed and Sealed this

Fourth Day of November, 1997

*Attest:*

BRUCE LEHMAN

*Attesting Officer*   *Commissioner of Patents and Trademarks*